United States Patent [19]

Crandall

[11] 4,009,720
[45] Mar. 1, 1977

[54] WEDGE SEAL FOR A TRACHEOTOMY TUBE

[75] Inventor: Norman C. Crandall, Diamond Bar, Calif.

[73] Assignee: Shiley Laboratories, Inc., Santa Ana, Calif.

[22] Filed: Aug. 14, 1975

[21] Appl. No.: 604,640

[52] U.S. Cl. .............................. 128/351; 285/334.2
[51] Int. Cl.² ........................................ A61M 25/00
[58] Field of Search .......... 128/351, 348, 349, 350, 128/214; 285/331, 110, DIG. 22, 319, 334.2, 334.3, 334.4, 200, 225

[56] References Cited
UNITED STATES PATENTS

| | | | |
|---|---|---|---|
| 2,310,944 | 2/1943 | Douglass | 285/334.2 |
| 3,169,529 | 2/1965 | Koenig | 128/351 |
| 3,688,774 | 9/1972 | Akiyama | 128/351 |
| 3,693,624 | 9/1972 | Shiley et al. | 128/351 |

Primary Examiner—Stephen C. Pellegrino
Attorney, Agent, or Firm—Knobbe, Martens, Olson, Hubbard & Bear

[57] ABSTRACT

A wedge-like seal for use with a tracheotomy tube having an inner cannula and an outer cannula. The seal is integrally formed within the outer end of the inner cannula to provide a tight seal engagement between the inner cannula and the outer cannula as well as between the coupling connector and the inner cannula. Incorporated in the seal is a circular sealing ridge from which depend two frusto-conical shaped sealing surfaces extending in opposite directions from the central ridge. The seal minimizes the force necessary to establish as well as to disengage the sealing contact between the respective tracheotomy tube parts, eliminating possible discomfort to the patient.

8 Claims, 4 Drawing Figures

WEDGE SEAL FOR A TRACHEOTOMY TUBE

BACKGROUND OF THE INVENTION

This invention relates to tracheotomy tubes and in particular to tracheotomy tubes that incorporates an annular cannula which can be removed for cleaning without removing the exterior of the trachea tube. Tracheotomy tubes have been used to provide a bypass supply of air to the patient when an obstruction occurs within the larynx or the pharynx area, the tracheotomy tube being inserted through an incision which is placed within he patient's neck below the obstructed area.

An important requirement is that the tracheotomy tube provides a bypass air supply to the patient while minimizing the discomfort borne by the patient. Not only is it, of course, desirable to minimize the pain which the patient must suffer, but in addition it is important to minimize movement of the outer cannular once it is installed in the patient's trachea. Otherwise, the trachea are may be irritated by abrasive movement of the outer cannula. Therefore, it is important that the inner cannula be attached and detached from the outer cannula with a minimum of force exerted upon the outer cannula. Also, it is important that the air connector be allowed a degree of rotational freedom relative to the inner and outer cannulae such that normal movement of the patient relative to the air line is tolerated without exerting any torque forces upon the outer cannula.

Heretofore, there has not been available a tracheotomy tube which maintains an air tight seal between both the inner and outer cannulae and between the inner cannula and the coupling connector while at the same time allowing for easy removability of the inner cannula as well as rotational movement of the air coupling with respect to the inner cannula. For example, the prior art includes sealing arrangements positioned at various locations along the trachea tube toward the distal end and are of such a tight nature that it is necessary to apply a significant amount of force to be able to remove the inner cannula from the outer cannula. Some prior art sealing arrangements use a ridge on the inner cannula which is of a greater diameter than the interior diameter of the outer cannula. This enlarged ridge is designed to snap into a recessed ring within the interior surface of the outer cannula. These prior art sealing arrangements require that a significant amount of force be exerted upon the inner cannula in order to remove it from the outer cannula. This force results in great discomfort to the patient and irritation to the trachea area, because the outer cannula is being moved and jerked during this sealing and unsealing process.

SUMMARY OF THE INVENTION

The present invention comprises a wedge-like seal having a central ridge circumferentially around the inner cannula from which depend two frusto-conical sealing surfaces in opposite directions to provide the necessary sealing of the gap between the inner cannula and the outer cannula as well as the gap between the inner cannula and the coupling. At least part of one of the frusto-conical sealing surfaces has a diameter which is greater than the diameter of the interior of the outer cannula, so that pressing the frusto-conical surface into the interior conduit or bore of the outer cannula will result in a tight engagement between the frusto-conical surface and the outer edge of the bore in the outer cannula. Similarly, a portion of the other frusto-conical sealing surface has a diameter greater than the internal diameter of the coupling connector adjacent its juncture with the outer cannula, so that movement of the coupling connector over the wedge seal will result in a tight air seal between the other frusto-conical sealing surface and the edge of the internal conduit of the connector coupling facing the outer cannula.

A significant feature of the present invention is that it seals the junction between the outer cannula and the coupling connector to prevent any leakage of either incoming or expelling air that may become entrapped in the gaps between the respective outer cannula and coupling with the inner cannula. An equally significant feature of the invention is that this air tight seal is effected with relative little force being required to attach the inner cannula to the outer cannula while essentially no force on the outer cannula is required to remove and unseal the inner cannula.

The novel tracheotomy tube seal disclosed herein also has the advantage of being compatible with a snap on connector such as we have disclosed in a patent application entitled "A Snap Lock Connector For A Tracheotomy Tube", applicant's attorney's docket number 2808, to be filed subsequently. As set out in this referenced patent application, the snap lock connector is designed to be able to axially rotate about both the inner and outer cannulae. This is an important feature necessary to the comfort of the patient, because when he is moving around in his bed, the air line connected to the connector sometimes twists which would tend to twist the tracheotomy tube in the patient's trachea causing discomfort. The frusto-conical shape of the sealing surface provides the ability for the connector to axially rotate while still maintaining the proper seal with the inner cannula.

DETAILED DESCRIPTION OF THE INVENTION

Figure 1:
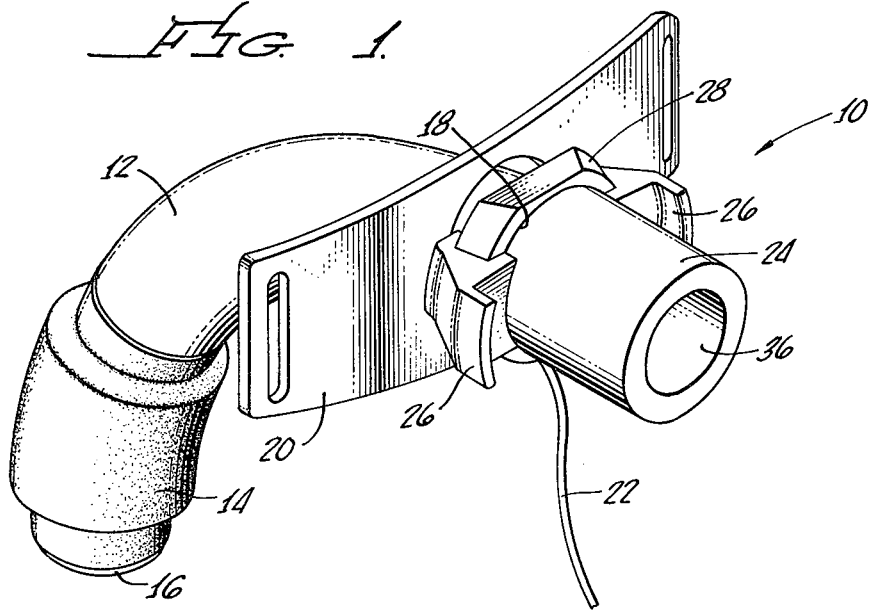
FIG. 1 is a perspective view of the tracheotomy tube assembly.

With respect to FIG. 1, a tracheotomy tube assembly 10 is shown with an outer cannula 12 and a sealing balloon 14 located adjacent the distal end 16 of the outer cannula 12. The sealing balloon 14 is advantageously constructed in accordance with the teachings of U.S. Pat. Nos. 3,659,612 and 3,693,624. Positioned adjacent the proximal end 18 of the outer cannula is a swivel neck flange 20 which is used to secure the assembly to the neck of the patient. A flexible inflation tube 22 extends from the proximal end 18 of the outer cannula to receive air to inflate the balloon 14 for sealing the outer cannula 12 within the trachea of the patient. Removably attached to the proximal end of the outer cannula 12 is a coupling or connector 24 having a pair of connection fingers 26 which are anchored on the rim 28 of the proximal end 18 of the outer cannula 12.

Figure 2:
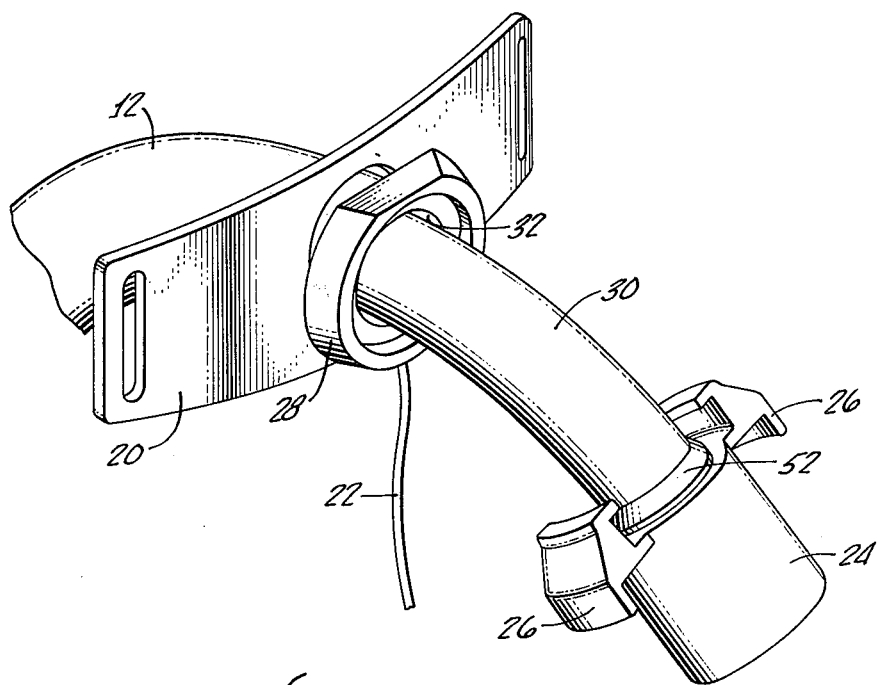
FIG. 2 is a perspective view of the tracheotomy tube assembly with the inner cannula partially removed.

FIG. 2 shows the inner cannula 30 partially removed from within the bore 32 of the outer cannula 12. The inner cannula 30 is designed to be completely removed from within the outer cannula 12 in order to cleanse the inner cannula periodically to provde a clean and clear passage for the flow of air to the patient. The coupling 24 in FIG. 3 is permanently affixed to the proximal end 34 of the inner cannula 30, but is able to axially rotate about the inner cannula in order to allow any twisting motion of the air supply line (not shown) which would be connected to the coupling 24 while not causing the twisting of the inner or outer cannula which are located in the patient's trachea.

Figure 3:
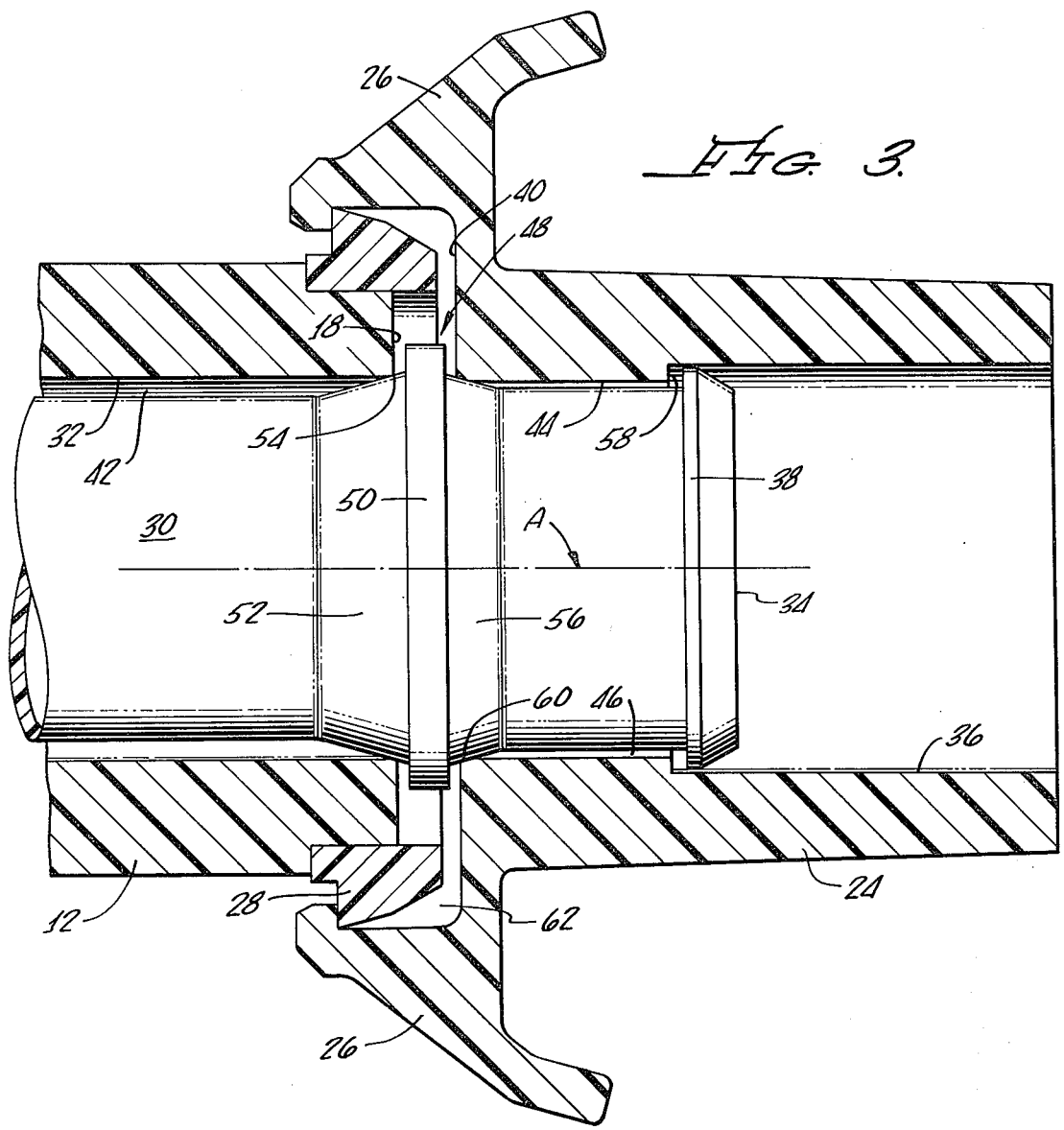
FIG. 3 is a partial sectional view through the coupling connector and the outer ends of the inner and outer cannulae.

The connection of the coupling 24 to the proximal end 34 of the inner cannula 30 is shown more clearly in FIG. 3. The coupling 24 has a conduit or passageway 36 which receives an air supply from an outside source. The bore or internal conduit 32 of the outer cannula 12 receives the inner cannula 30. It should be noted that the inner conduit 34 of the inner cannula 30. This is in order to allow for the anchoring of the retaining ring 38 at the proximal end 34 of the inner cannula. Consequently, the proximal end 34 of the inner cannula 30 is permanently connected to the cannula end 40 of the coupling 24.

It should be noted that the exterior diameter of the inner cannula 30 is less than the diameter of the bore or conduit 32 of the outer cannula 12. Consequently, there is a small circumferential gap 42 which exists between the interior surface of the bore 32 of the outer cannula 12 and the exterior surfaces of the inner cannula 30. Similarly, the exterior diameter of the inner cannula 30 is less than the inner diameter of the necked down portion 44 of the conduit 36 in the coupling 24, so that there is a small circumferential gap 46 which exists between the coupling 24 and the inner cannula 30.

Integrally formed on the inner cannula 30 adjacent the proximal end 34 is wedge-like double surfaced seal 48. The seal is comprised of a main ring or ridge 50 which circumferentially surrounds the inner cannula 30 and has an exterior diameter which is greater than either the interior diameter of the conduit which is greater than either the interior diameter of the conduit 32 in the outer cannula 12 or the diameter of the interior conduit 44 of the coupling 14. The seal 48 is preferably made of clear polypropylene and it is preferably molded integrally within the inner cannula 30 adjacent its proximal end 34. Extending from one side of the ring 50 toward the outer cannula 12 is a frusto-conical surface 52 extending in a longitudinal direction with respect to the inner cannula 30. It should be noted that at least a portion of the frusto-conical or wedge-like sealing surface 52 has an exterior diameter which is greater than the interior diameter of the bore 32 of the outer cannula 12. Consequently, as the surface 52 is moved into the bore 32, the proximal edge 54 of the conduit 32 will seal tightly against the surface 52.

Extending in a direction opposite from the central ring 50 in a direction toward the connector 24 is a second frustoconical sealing surface 56 of which at least a portion has a greater diameter than the diameter of the necked down conduit 44 of the coupling 24. Therefore, the movement of the cannula side edge 60 of the conduit portion 44 onto the wedge-like sealing surface 56 will result in a tight seal between the coupling 24 and the inner cannula 30. The ring 50 acts as a guard to prevent the insertion of the inner cannula 30 into the outer cannula 12 from being beyond the sealing surface 52. Similarly, the ring 50 prevents the coupling 24 from going beyond the sealing surface 56 when the coupling is moved onto the proximal end 34 of the inner cannula.

Figure 4:
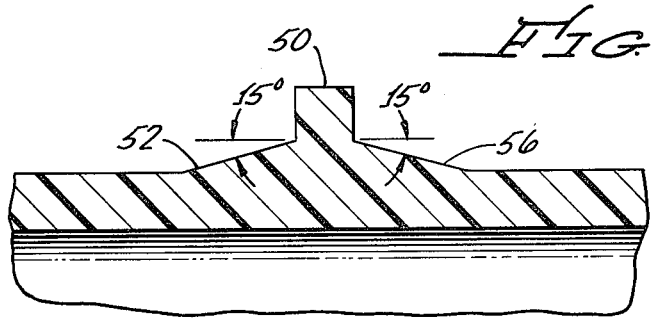
FIG. 4 is a sectional view through a portion of the seal.

It has been determined with respect to the slope of the sealing surface 52 and 56 that an angle of fifteen degrees with respect to the longitudinal axis A of the proximal end of the inner cannula is a satisfactory incline. The slope of the sealing surface is shown more clearly on FIG. 4. If the angle were made too large, the desired wedge-like seal operation would be lost. On the other hand, if the angle is too small, the sealing surfaces would become longer than desired. Because tracheotomy tubes are made of various sizes to accommodate various individuals, the sealing surface 52 may extend down from the central ridge 50 at a greater radial distance on the central ridge than the other sealing surface 56 as shown in FIG. 4.

Turning to the procedural use of the present invention, reference is made to FIGS. 1 through 3. The outer cannula 12 is placed in the patient's trachea. The inner cannula 30 with the coupling 24 is inserted into the bore 32 of the outer cannula located in the patient's trachea. The coupling 24 is free to axially rotate about the longitudinal axis A of the proximal end 34 of the inner cannula 30. The inner cannula is inserted into the outer cannula far enough so that the connecting fingers 26 can hook over the restraining surface 62 of the rim 28. However, coincidentally with the hooking of the fingers 26 over the rim 28 is the sealing contact of not only the proximal edge 54 of the bore 32 with the one sealing surface 52, but also the cannula facing edge 60 of the coupling 24 with the other sealing surface 56. This sealing operation is similar in principle to inserting a cone into the end of a tube to plug the end of the tube with the diameter of part of the cone being greater than the diameter of the tube. In order to accomplish this sealing engagement some slight force is directed toward the proximal end 18 of the outer cannula. However, because the swivel neck flange 20 receives this force and distributes it over the large area of the patient's outer neck surface, there is no discomfort to the patient. The patient's trachea receives no irritating movement of the outer cannula.

When the inner cannula 30 is to be removed from within the outer cannula 12, the locking or connecting fingers 26 are pivotally disengaged from the surface 62 of the rim 28 and the inner cannula 30 is simply withdrawn. The patient does not experience any forces which would tend to move the outer cannula and cause discomfort.

Consequently, as a result of the above unique sealing arrangement, the air which is introduced to the inner cannula from the outside air source through the coupling 24 will not leak at the junction of the inner cannula and the coupling. The tight seal between the sealing surface 56 and the edge 60 will prevent any flow of air leaking through the gap 46 and out into the area 62 between the coupling 24 and the outer cannula 12. Also any air which enters the gap 42 between the inner cannula 30 and the outer cannula 12 from the distal end of both cannulas will be prevented from flowing into the area 62 because of the tight seal between the sealing surface 52 and the edge 54.

What is claimed is:
1. A tracheotomy tube comprising:
an outer cannula;
a removable inner cannula;
a coupling to an outside fluid supply;

a first wedge-like sealing surface of plastic material located adjacent one end of said inner cannula, said sealing surface sloping radially away from the exterior of said inner cannula in a direction along said inner cannula; and a second wedge-like sealing surface of plastic material located adjacent said first wedge-like sealing surface and sloping radially away from the exterior surface of said inner cannula in a direction opposite said direction of said wedge-like sealing surface along said inner cannula;

an internal edge on the end of said outer cannula bearing on said first wedge-like sealing surface and flexing under only slight axial, nonrotational force to seal said inner cannula with said outer cannula; and an internal edge on said coupling bearing on said second wedge-like sealing surface and flexing under only slight axial, non-rotational force to seal said coupling with said inner cannula when said inner cannula is positioned completly within said outer cannula.

2. a tracheotomy tube comprising:
an outer cannula;
a removable inner cannula;
a coupling to an outside fluid supply;
a frusto-conical sealing surface located on the proximal end of said inner cannula, said sealing surface sloping radially away from the exterior surface of said inner cannula, said sealing surface facing said outer cannula and having at least one diameter which is greater than the interior diameter of said outer cannula;
an internal edge on said outer cannula bearing on said sealing surface and flexing under slight axial force to establish sealing engagement of said inner cannula with said outer cannula when the proximal end of said outer cannula receives said coupling, movement of said inner cannula into said sealing engagement and movement of said inner cannula out of said sealing engagement causing no irritational movement of said outer cannula in a patient's trachea.

3. a tracheotomy tube comprising:
an outer cannula;
a removable inner cannula;
a coupling to an outside fluid supply;
a frusto-conical sealing surface located on the proximal end of said inner cannula, said sealing surface sloping radially away from the exterior surface of said inner cannula, said sealing surface facing said coupling and having at leas tone diameter which is greater than the interior diameter of said coupling;
an internal edge of said coupling bearing on said sealing surface and flexing under slight axial force to establish sealing engagement of said inner cannula with said coupling when the proximal end of said outer cannula receives said coupling, movement of said coupling into said sealing engagement and movement of said coupling out of said sealing engagement causing no irritational movement of said outer cannula in a patient's trachea.

4. a tracheotomy tube comprising:
an outer cannula having an internal, annular edge;
a coupling to an outside fluid supply having an internal, annular edge; and
a removable inner cannula comprising:

a junction ridge circumferentially surrounding the exterior surface of said inner cannula, said ridge having an exterior diameter greater than the interior diameter of said outer cannula and greater than the interior diameter of said coupling;
a first wedge-like sealing surface sloping from one side of said ridge to the exterior surface of said inner cannula; and
a second wedge-like sealing surface sloping from the other side of said ridge to the exterior surface of said inner cannula, said first sealing surface contacting said annular edge of said outer cannula to seal a circumferential gap between said inner cannula and said outer cannula, said second sealing surface contacting said annular edge of said coupling to seal a circumferential gap between said inner cannula and said coupling when said inner cannula is within said outer cannula and said coupling is attached to said inner and outer cannulae.

5. A tracheotomy tube as defined in claim 4 wherein said first and second wedge-like sealing surfaces are frusto-conical surfaces.

6. A tracheotomy tube as defined in claim 5 wherein said slope of said frusto-conical surfaces is 15° with respect to the longitudinal axis of the proximal end of said inner cannula.

7. A tracheotomy tube for insertion through an incision in a patient's neck into the trachea to support breathing, said tube comprising:
an outer cannula having a first end for placement within said trachea and a second end for placement outside said trachea, said second end including an annular, internal edge;
an inner cannula inserted into the bore of said outer cannula, said inner cannula being removable from said outer cannula to permit removal of obstructions from said tracheotomy tube;
a connector secured to said inner cannula adjacent said second end of said outer cannula said connector including an annular, internal edge; and
a dual wedge seal connected to said inner cannula adjacent said second end, said dual wedge having a first frusto-conical surface facing toward said edge of said outer cannula and a second frusto-conical surface facing toward said edge of said connector, at least one diameter of said first frusto-conical surface being larger than the diameter of said outer cannula edge and at least one diameter of said second frusto-conical surface being larger than the diameter of said connector edge, so that said dual wedge seal will seal against said outer cannula edge and said connector edge by a minimal force on said second end of said outer cannula toward said patient's neck without causing any irritating movement of said outer cannula within said trachea and so that removal of said dual wedge seal from sealing contact with said outer cannula and said connector will not cause movement of said outer cannula within said trachea.

8. A tracheotomy tube for introducing a supplemental fluid to a patient's trachea, said tube comprising:
an outer cannula having a distal end and a proximal end;
an inner cannula inserted into the bore of said outer cannula, said inner cannula having a proximal end and a distal end;

a coupling rotatably mounted permanently on said proximal end of said inner cannula and establishing a passageway, said coupling rotatable axially with respect to the longitudinal axis of said proximal end of said cannula, one end of said coupling connected to a supply line of said supplemental fluid said coupling having an internal, annular edge; and a wedge seal located on said proximal end of said inner cannula, said seal having a frusto-conical sealing surface facing toward said coupling edge, at least one diameter of said frusto-conical surface being larger then the diameter of said coupling edge, said sealing surface establishing a tight seal with said one end of said passageway in said coupling, said sealing surface maintaining said tight seal while allowing said coupling to axially rotate with respect to said sealing surface as a result of said patient inadvertently placing a torque on said supply line without rotating said inner or outer cannulae.

* * * * *

UNITED STATES PATENT OFFICE
CERTIFICATE OF CORRECTION

PATENT NO. : 4,009,720
DATED : March 1, 1977
INVENTOR(S) : Norman C. Crandall

It is certified that error appears in the above-identified patent and that said Letters Patent are hereby corrected as shown below:

Column 1, line 6, change "incorporates" to ---incorporate---
line 19, change "cannular" to ---cannula---; line 21, change "are" to ---area---; line 67, change "the" to ---that---.

Column 3, line 18, after "conduit", insert ---36 of the coupling 24 is necked down adjacent the proximal end---; line 29, change "surfaces" to ---surface---; line 40, after "diameter", delete "which is greater than either the interior diameter of the conduit"; line 44, change "14" to ---24---; line 67, change "being" to ---going---.

Column 5, line 4, after "exterior", insert ---surface---;

line 53, delete "leas tone" and insert ---least one---;

Signed and Sealed this fifth Day of July 1977

[SEAL]

Attest:

RUTH C. MASON
Attesting Officer

C. MARSHALL DANN
Commissioner of Patents and Trademarks